(12) United States Patent
Wu

(10) Patent No.: US 10,793,876 B2
(45) Date of Patent: Oct. 6, 2020

(54) RETRO- AND LENTI-HBV HYBRID VECTORS AND CONSTRUCTS

(71) Applicant: VIRONGY L.L.C., Manassas, VA (US)

(72) Inventor: Yuntao Wu, Manassas, VA (US)

(73) Assignee: VIRONGY L.L.C., Manassas, VA (US)

(*) Notice: Subject to any disclaimer, the term of this patent is extended or adjusted under 35 U.S.C. 154(b) by 0 days.

(21) Appl. No.: 16/474,661

(22) PCT Filed: Dec. 28, 2017

(86) PCT No.: PCT/US2017/068766
§ 371 (c)(1),
(2) Date: Jun. 28, 2019

(87) PCT Pub. No.: WO2018/126042
PCT Pub. Date: Jul. 5, 2018

(65) Prior Publication Data
US 2019/0330656 A1   Oct. 31, 2019

Related U.S. Application Data

(60) Provisional application No. 62/440,064, filed on Dec. 29, 2016.

(51) Int. Cl.
*C12N 15/86* (2006.01)
*C12N 7/00* (2006.01)

(52) U.S. Cl.
CPC .............. *C12N 15/86* (2013.01); *C12N 7/00* (2013.01); *C12N 2730/10121* (2013.01); *C12N 2740/16043* (2013.01)

(58) Field of Classification Search
None
See application file for complete search history.

(56) References Cited

U.S. PATENT DOCUMENTS

| 5,958,768 A | 9/1999 | Kraus et al. |
| 6,610,471 B1 * | 8/2003 | Isom ............ C12Q 1/706 435/370 |

FOREIGN PATENT DOCUMENTS

WO    2015175380 A1    11/2015

OTHER PUBLICATIONS

Arthur Z. Zelent et al., "Replicative Intermediate of Hepatitis B Virus in Transfected Murine Fibroblasts," Journal of Virology, Sep. 1987, pp. 2,921-2,923, vol. 61, No. 9.
Jianhong Chen et al., "Characterization of Novel Hepatitis B Virus PreS/S-Gene Mutations in a Patient with Occult Hepatitis B Virus Infection," PLoS One, May 16, 2016, pp. 1-14, vol. 11, No. 5.
International Search Report and Written Opinion for PCT/US2017/068766, dated Mar. 7, 2018.

* cited by examiner

*Primary Examiner* — Nicole Kinsey White
(74) *Attorney, Agent, or Firm* — Pilloff Passino & Cosenza LLP; Sean A. Passino; Rachel K. Pilloff

(57) ABSTRACT

The present disclosure relates to the design of a retro- or lenti-viral HBV (hepatitis B virus) hybrid vector for delivery of HBV genomes into cells such as liver cells. Provided herein are design, methodology, compositions, and the like for such vectors for delivering HBV genes or genomes into cells for anti-HBV drug screening, HBV research, or test of anti-HBV therapeutics.

9 Claims, 8 Drawing Sheets

Specification includes a Sequence Listing.

(A)

(B)

RETRO- AND LENTI-HBV HYBRID VECTORS AND CONSTRUCTS

CROSS-REFERENCE TO RELATED APPLICATION

This application claims benefit of U.S. Provisional Application No. 62/440,064, filed Dec. 29, 2016, which application is incorporated herein by reference in its entirety.

FIELD

The present disclosure relates to the design of a retro- or lenti-viral HBV (hepatitis B virus) hybrid vector system for the delivery of the HBV genome into cells such as liver cells. Provided herein are design, methodology, compositions, and the like for such vectors for the delivery of HBV genes or genome into cells for anti-HBV drug screening, HBV research, or test of treatment.

INTRODUCTION

Hepatitis B virus (HBV) infects liver cells that cause both acute and chronic infections. The virus is a member of the hepadnavirus family. HBV virion particles are enveloped, and are 30-42 nm in diameter. Infectious HBV particles are called "Dane particles" that can infect hepatocytes or liver cells. The viral genome is double-stranded circular DNA with single-stranded DNA regions. The viral genome is 3020-3320 nucleotides long for the full-length strand (or the "−" sense strand), and 1700-2800 nucleotide long for the short length-strand (or the "+" sense strand). One end of the full-length strand is also linked to the viral DNA polymerase that has reverse transcriptase activity. The partially double-stranded DNA is rendered fully double-stranded (or called cccDNA, covalently closed circular DNA) following viral DNA entry into the nucleus. The viral genome can transcribe four genes, known as C, X, P, and S. The gene C codes for viral core protein (HBcAg); the P gene codes for the DNA polymerase; the S gene is the gene that codes for the surface antigen (HBsAg); the X gene codes for the X protein whose function is not fully understood.

HBV infects cells through specific receptors such as the liver-specific bile acid transporter named the sodium taurocholate cotransporting polypeptide (NTCP). HBV has been known to have low infectivity for cultured live cell lines such as HepG2, which can be complemented with the NTCP receptor to enhance viral entry. The limited entry and low infectivity of HBV in cell culture conditions frequently pose limitations to HBV research, anti-HBV drug discovery, and the test of therapeutics.

Retroviral vectors such as the Moloney murine leukemia virus-based vectors are one the most common vector systems for gene delivery and gene therapy. The vectors can be assembled into infectious but replication-defective particles for the transduction of many cell types. Retroviral particles contain a RNA genome, which is reverse transcribed by the virion reverse transcriptase into double-stranded DNA once inside the cells. The DNA can then integrate into a cell's genome for persistent gene expression. For retroviral vectors, the typical length allowed for a foreign DNA insert is usually 8-10 kb.

Lentiviral vectors are a subclass of Retroviral vectors. Lentiviral vectors share many similarities with retroviral vectors. The viral RNA genome is also revere-transcribed into DNA and then inserted into a cell's genome. The main difference between retroviral vectors and lentiviral vectors is that lentiviruses are capable of infecting non-dividing and actively dividing cell types, whereas retroviruses can only infect mitotically active cell types.

To produce a retro- or lentiviral particle, several plasmids are normally required to cotransfect a so-called packaging cell line, commonly HEK293 cells. One or more plasmids, generally referred to as packaging vectors, encode virion structural proteins such as the capsid, the reverse transcriptase, the integrase, and other virion proteins. Another plasmid contains the genetic material to be delivered by the vector. It contains the gene of interest and the ψ (psi) sequence which is used to package the RNA genome into the virion. In addition, a plasmid that encodes an envelope protein such as the VSV glycoprotein (the vesicular stomatitis virus G-protein) is normally used to mediate viral entry into cells of interest. The use of a non-retroviral envelope protein is called pseudotyping. The VSV-G pseudotyping is widely used for the infection of multiple cell types because of its broad tropisms.

Retro- and lentiviral vectors can either integrate or non-integrate into a cell's genome. The non-integrating vector is normally constructed through the use of integrase mutants such as the D116N integrase mutation in HIV. The non-integrating vector can also deliver genes for short period of expression in dividing cells, and for long-term gene expression in non-dividing cells.

SUMMARY

In one aspect, provided herein are design, compositions, and methodology for construction of a Retro- or Lenti-viral HBV hybrid viral vector for the delivery of HBV genomes into cells such as hepatocytes. Such a system has a Retro- or Lenti-viral particle on the outside, permitting effective entry and infection of liver cells or other cell types. Inside the particle, the viral genome packaged is mainly the HBV genome. In one embodiment, an HBV genome such as the HBV 1.3-mer replicon genome is combined with genomic fragments from retro- or lenti-viruses to construct a hybrid genomes (FIG. 1). Such genome contains the retro- or lenti-viral LTR (long terminal repeat) at both ends, the retro- or lenti-viral ψ (psi) sequence which is used to package the RNA genome into the retro- or lenti-viral virion. The hybrid genome may also contain additional element such as the HIV RRE (Rev-dependent element) to facilitate genome packaging. A full HBV replicon genome (1.3 mer replicon) or a partial HBV gene expressing limited number of HBV genes such as the C, P, X, or S genes can be inserted in the middle, in either orientation. The HBV genes can be expressed using their own promoters in the HBV genome.

In another aspect, the LTR can be a SIN LTR (A self-inactivating LTR with ΔU3 deletion) (FIG. 1C)

In another aspect, an origin of DNA replication such as the OriP/EBNA-1 from EBV (Epstein-Barr virus) or SV40 (SV40 Ori) can be inserted into the vector which will permit the self-duplication of the circular DNA with cell division, permitting its persistence in dividing cells (FIG. 1D).

In another aspect, the Retro- or Lenti-HBV hybrid vector can be assembled into a retro- or Lenti-viral particles through the using of packaging vectors that encode the retro- or lenti-virion structural proteins, such as the capsid, the reverse transcriptase, the integrase, and other virion proteins. Such a hybrid vector is assembled into a retro- or lenti-viral particle that can be used to infect liver cells or other cell types (FIG. 2).

The hybrid vector can also be assembled into a non-integrating particle through the use of integrase mutants such as the HIV integrase D116N mutant. Such non-integrating vector promotes the formation of covalently closed circular DNA (called 1-LTR circle and 2-LTR circles) in cells following transduction, mimicking the HBV cccDNA (FIG. 3).

In another aspect, such a Retro- or Lenti-HBV system can be used to deliver a defective HBV genomes such as the HBV genome with the mutation of the X gene or the S gene. Such system can be completed by providing the missing genes. Anti-HBV drugs targeting the missing genes can be screened in such a system (FIG. 4)

In another embodiment, the hybrid vector also contains all HBV genes necessary for the assembly of HBV viron particles, and can assemble into HBV particles when transfected into suitable cells such as hepatocytes. When retro- or lenti-viral packaging plasmids were provided, both retro- or lenti-viral particles and HBV particles are assembled in the system, generating two types of virion particles (FIG. 5).

In another embodiment, the hybrid vector is embedded into a cell's genome. Cells harboring the Retro- or Lenti-viral HBV hybrid DNA construct can be used as a platform for constitutive production of HBV viral particles, or can be used as a platform for anti-HBV drug screening (FIG. 6). The Retro- or Lenti-HBV hybrid genome can also be defective in HBV genes such as the HBV X gene or the P gene. These defects can be complemented by providing the X gene or the P gene through DNA transfection or viral vector transduction of a DNA construct expressing the X or the P gene. Such system can be used to screen drugs again the X or the P protein.

DETAILED DESCRIPTION

Figure 1:
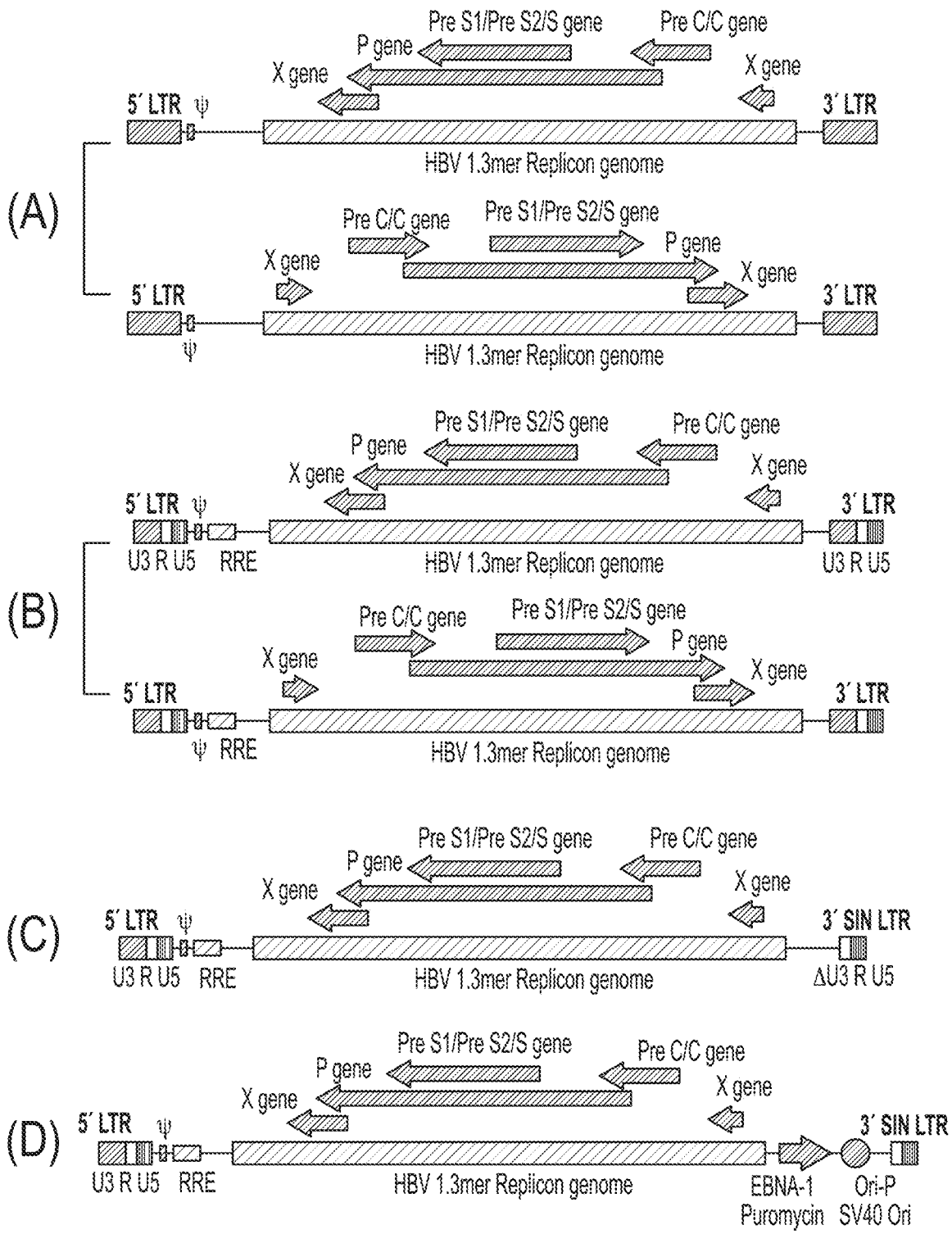
FIG. 1: Schematic representation of the Retro- or Lent-viral HBV hybrid vectors. (A) Schematic representation of a Retro-viral HBV hybrid vector. Shown are the Retroviral vector 5' LTR, 3' LTR, the packaging signal ψ (psi) sequence, and the HBV 1.3mer replicon genome in two orientations. (B) Schematic representation of Lenti-viral HBV hybrid vector. Shown are the Retroviral vector 5' LTR, 3' LTR, the packaging signal ψ (psi) sequence, the RRE (Rev responsive element), and the HBV 1.3mer replicon genome in two orientations. (C) Schematic representation of Lenti-viral HBV hybrid vector with a SIN LTR. Shown are the Retroviral vector 5' LTR, the packaging signal ψ (psi) sequence, RRE, the 3' SIN LTR, and the HBV 1.3mer replicon genome. (D) Schematic representation of a Lenti-viral HBV hybrid vector with an origin of DNA replication or selection marker gene. Shown are the Retroviral vector 5' LTR, the packaging signal ψ (psi) sequence, RRE, the 3' SIN LTR, and the HBV 1.3mer replicon genome, an origin of DNA replication (examples are the Ori-P from EBV or SV40 Ori). The vector may also contain additional genes such as the EBNA-1 gene from EBV to support DNA replication or a selection marker gene such as puromycin-resistant gene for selection of cells harboring the construct. These genes are expressed from a separate promote such as the commonly used CMV promoter.
Figure 2:
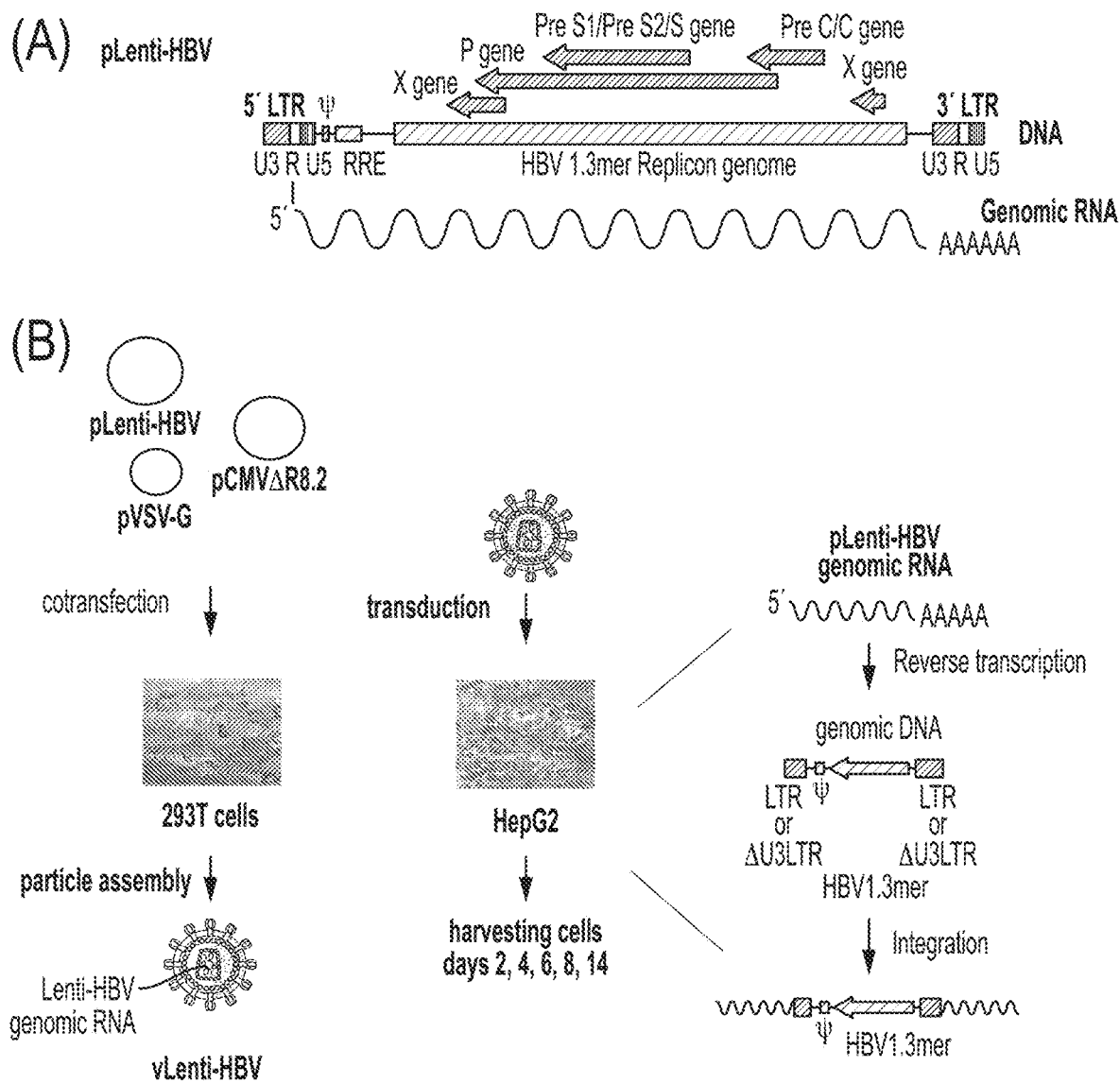
FIG. 2: Assembly of the Retro- or Lenti-viral hybrid vector and its use in transducing cells. (A) When transfected into a packaging cell line such as HEK293T, the hybrid vector can transcript a genomic RNA that contains the HBV genome. This genomic RNA can also be packaged into a Retro- or Lenti-viral particle through the help of packaging vectors expression retro- or lenti-viral structural proteins. (B) Shown is an example of the assembly of a lenti-viral HBV hybrid particle by cotransfection of 293T cells with three plasmids: the pLenti-HBV hybrid vector that provides the genomic RNA for packaging, the pCMVΔR8.2 provides structural proteins, such as the capsid, the reverse transcriptase, the integrase, and other virion proteins. The pVSV-G vector provide VSV-G envelope protein for viral entry into multiple cell types. The Lenti-viral HBV hybrid particle can be used to transduce hepatocytes such as HepG2 cells. Once inside the cells, the lenti-HBV viral genome is reverse transcribed into double-stranded DNA, and integrates into a cells' genome. The HBV gene can be expressed from the Lenti-viral HBV genome.
Figure 3:
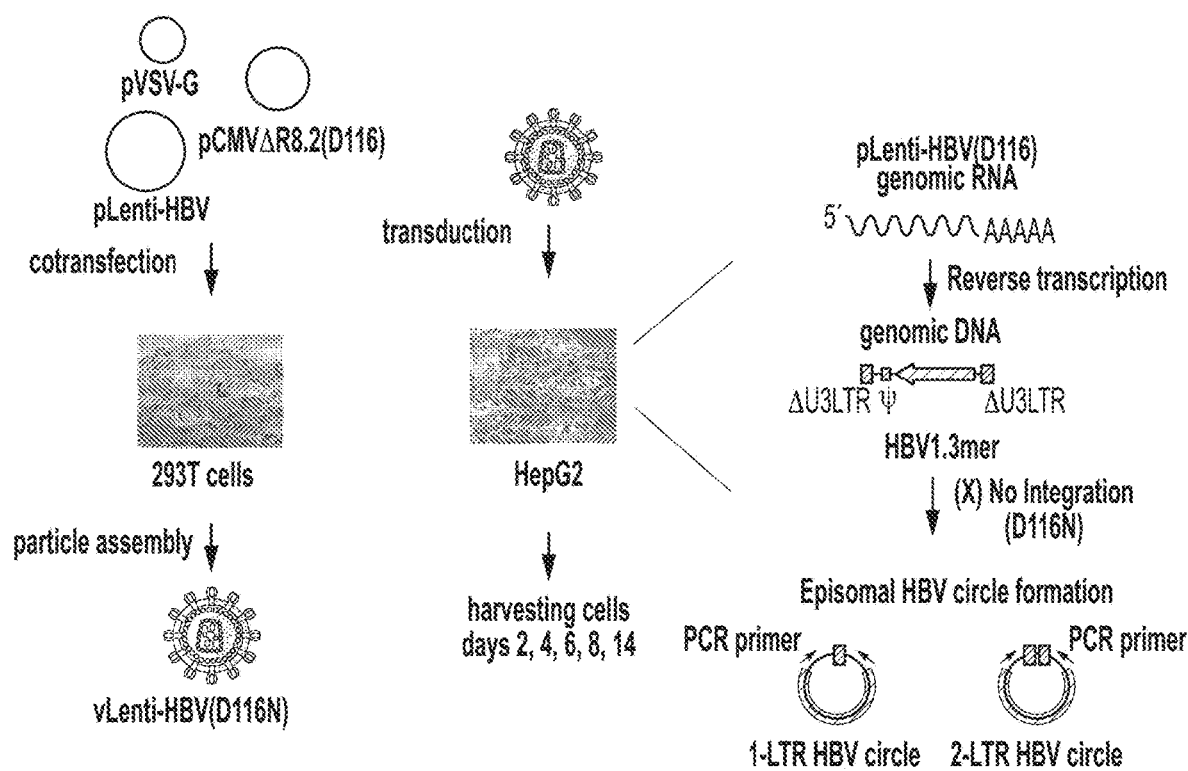
FIG. 3: Assembly of a non-integrating Retro- or Lenti-viral hybrid vector and its use in transducing cells. The Retro- or Lenti-viral HBV hybrid vector can also be assembled into a non-integrating particle through the use of a packaging vector carrying an integrase mutation, such as the HIV integrase D116N mutant. Such a packaging plasmid is shown as the pCMVΔR8.2 (D116N). The non-integrating hybrid vector promotes the formation of covalently closed circular DNA (called 1-LTR circle and 2-LTR circles) in cells following transduction. These circles resemble HBV cccDNA.
Figure 4:
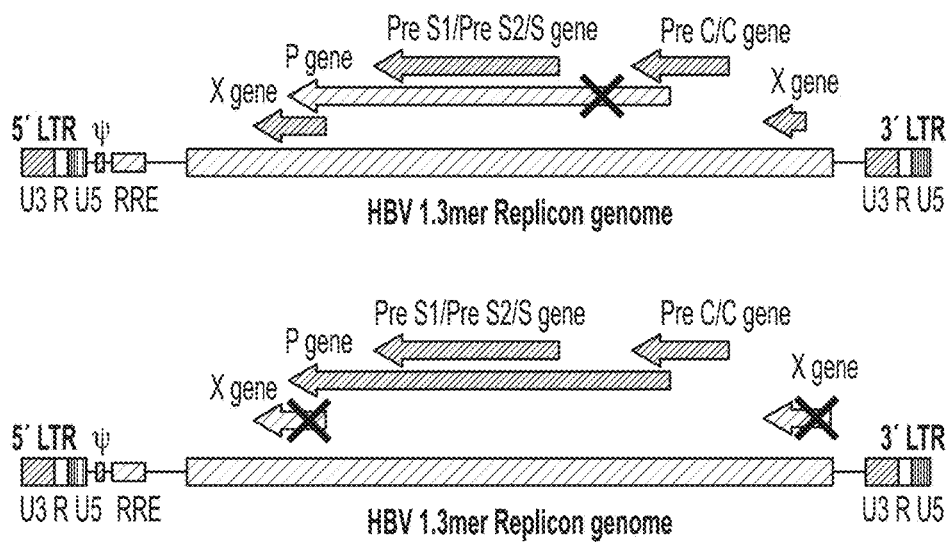
FIG. 4: Assembly of a Retro- or Lenti-viral hybrid vector with defective HBV genomes and its use in HBV research and drug discovery. The Retro- or Lenti-HBV hybrid vector can be used to deliver a defective HBV genome such as the HBV genome with the mutation of the X gene or other genes such as the P gene. Such a system can be complemented by providing the missing genes through DNA transfection or additional viral vector transduction. Anti-HBV drugs targeting the missing genes can be screened in such a system.
Figure 4:
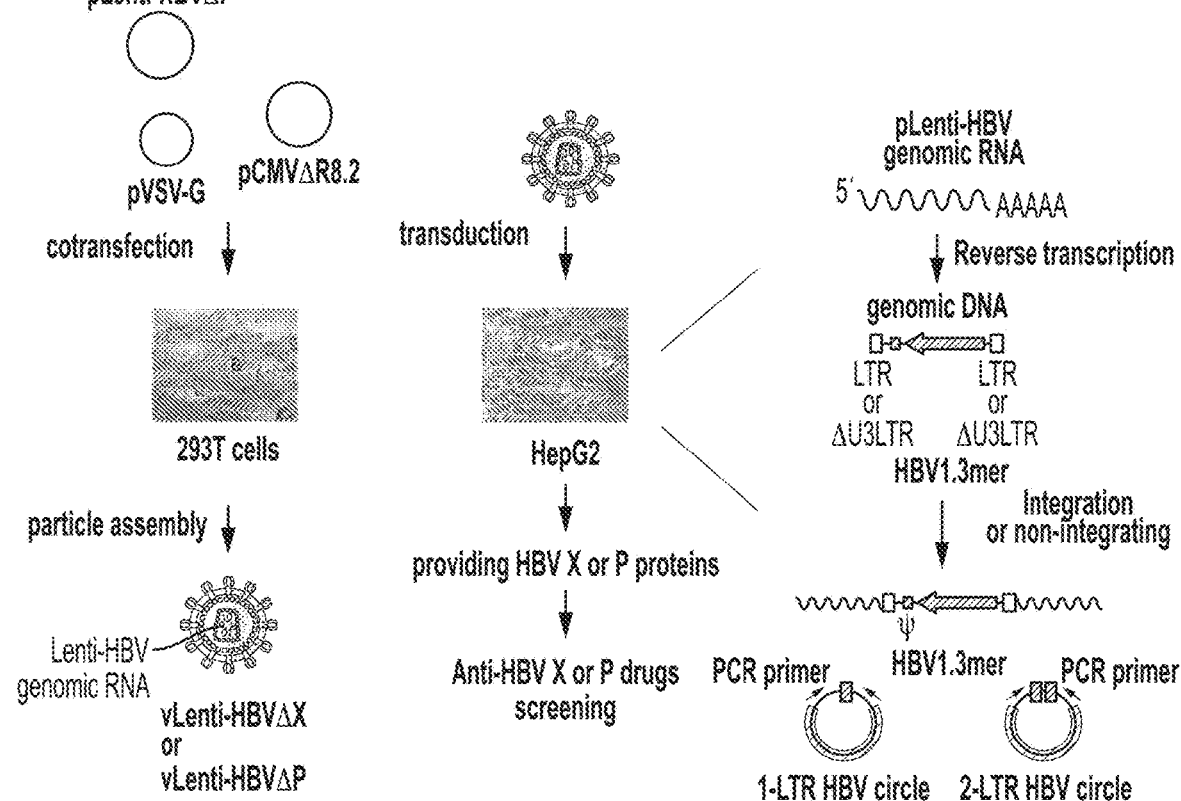
Figure 5:
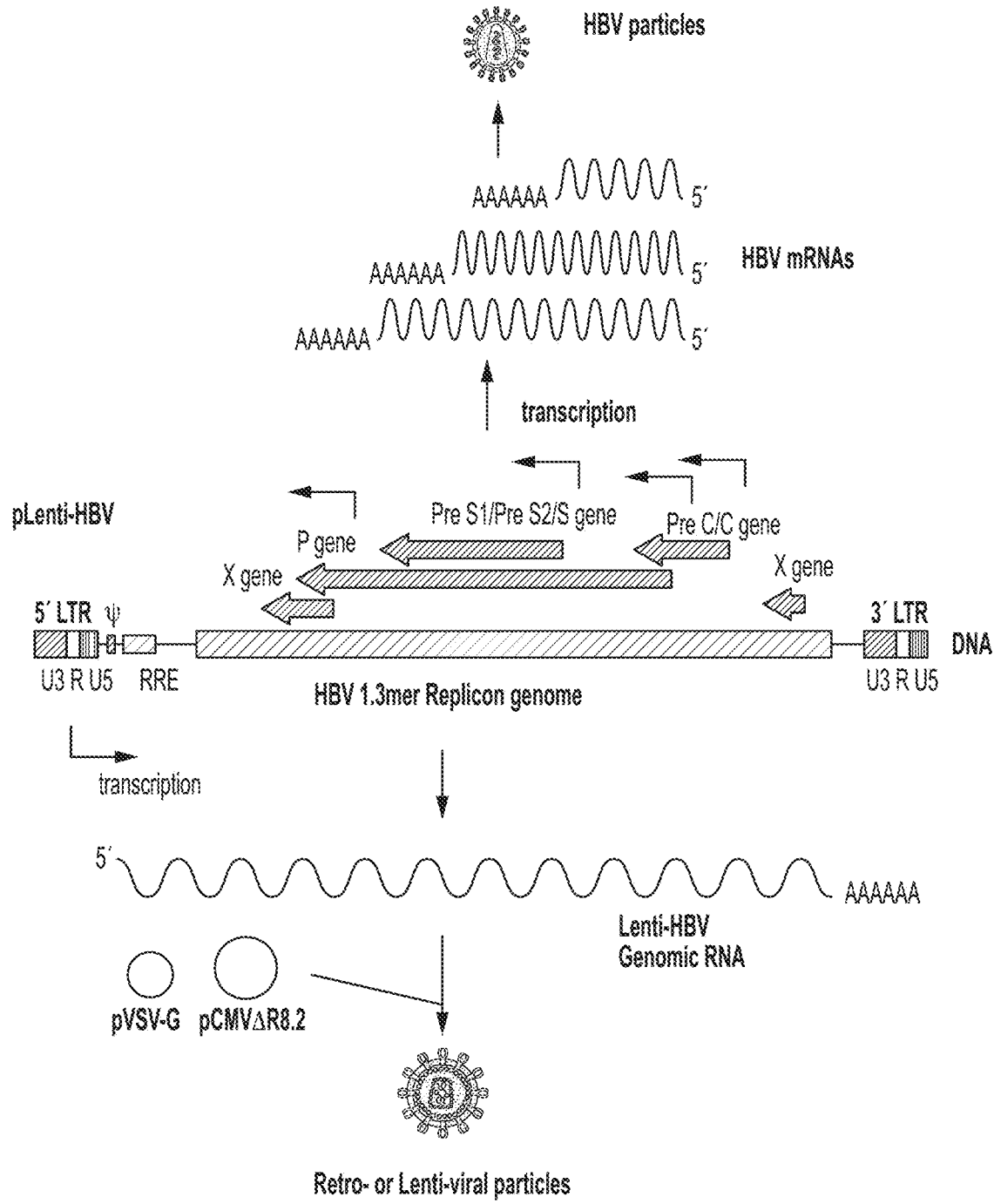
FIG. 5: The ability of the Retro- or Lenti-viral HBV hybrid vector in producing HBV particles and lentiviral particles. The hybrid vector contains all HBV genes necessary for the assembly of HBV viron particles, the hybrid vector is able to assemble HBV particles when transfected into suitable cells such as hepatocytes. When retro- or lenti-viral packaging plasmids were provided (such as pCMVΔR8.2 and pVSV-G), both retro- or lenti-viral particles and HBV particles are assembled in the system, generating two types of virion particles.
Figure 6:
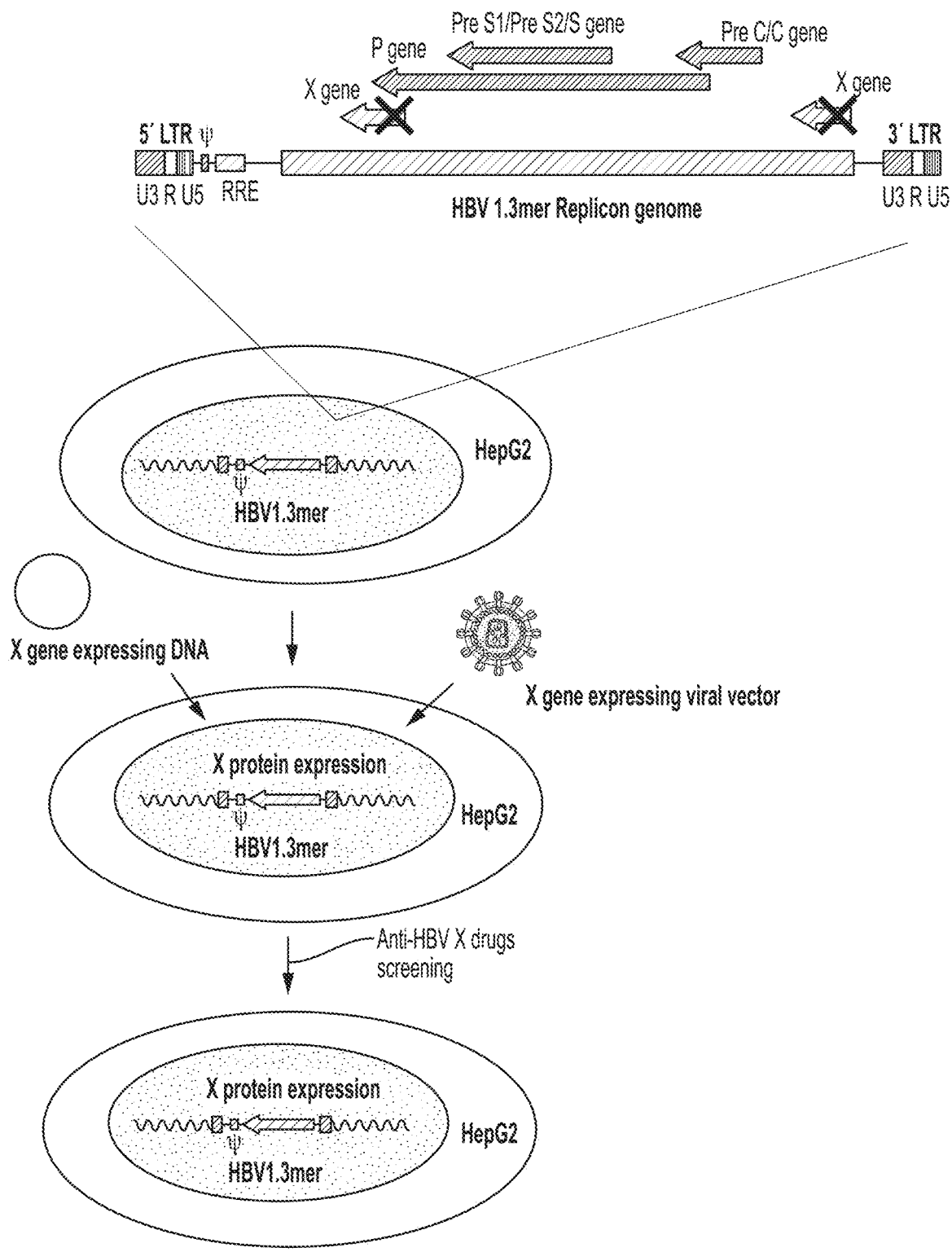
FIG. 6: Engineered cell lines carrying the Retro- or Lenti-viral HBV hybrid construct. The Retro- or Lenti-viral HBV hybrid vector can be embedded into a cell's genome, either through standard DNA transfection or viral vector transduction. Cells harboring the Retro- or Lenti-viral HBV hybrid DNA construct can be used as a platform for constitutive production of HBV viral particles, or can be used as a platform for anti-HBV drug screening. As exemplified here, the Retro- or Lenti-viral HBV hybrid genome contains the HBV genome with mutations in the HBV X gene. The X gene defect can be complemented by providing the X gene through DNA transfection or viral vector delivery of a DNA construct expressing the X gene. Such system can be used to screen drugs against the X protein. Such drugs can prevent the complementation of HBV functions by the X protein.

The present disclosure relates to design, methodology, and compositions for construction of a Retro- or Lenti-viral HBV hybrid viral vector system for the delivery of HBV genome into cells such as hepatocytes. In one embodiment, an HBV genome such as the HBV 1.3-mer replicon genome is combined with genomic fragments from retro- or lenti-viruses to construct a hybrid genomes. Such genome contains the retro- or lenti-viral LTR (long terminal repeat) at both ends, the retro- or lenti-viral ψ (psi) sequence which is used to package the RNA genome into the retro- or lenti-viral virion. The hybrid genome may also contain additional element such as the HIV RRE (Rev-dependent element) to facilitate genome packaging. A full HBV replicon genome (1.3 mer replicon) or a partial HBV genome expressing limited number of HBV genes such as the C, P, X, or S genes can be inserted in the middle, in the reverse orientation in transcription to the promoter of (LTR) retro- or Lenti-viral genome. The HBV genes can be expressed using their own promoters in the HBV genome from the opposite orientation to the retro- or lenti-viral transcription.

The present inventors realized that an instant retro- or lenti-vector uses 5' LTR to 3' LTR transcription orientation, which is in the reverse orientation to the HBV genome transcription as arranged and inserted. This reverse transcription arrangement allows the assembly and packaging of a complete HBV genomes into a retro- or lenti-viral particle, as this arrangement avoids the use of multiple functional poly(A) termination signals present in the HBV genome. Conversely, if the HBV genome is inserted into the retro- or lenti-viral vector in the same transcriptional orientation, the presence of HBV poly(A) signals would prematurely terminate the 5' LTR transcription from the retro- or lenti-viral vector for a full length mRNA, thus preventing the HBV genome from being packaged into retro- or lenti-viral particles.

In one embodiment, the Retro- or Lenti-HBV hybrid vector can be assembled into a retro- or Lenti-viral particles through the using of packaging plasmids that encode the retro- or lenti-viral structural proteins, such as the capsid, the reverse transcriptase, the integrase, and other virion proteins. The particle can also be pseudotyped with envelope proteins such as VSV-G, HIV gp120, HBV S proteins, or viral envelope proteins from other viruses (HDV, measles virus et al).

In another embodiment, the hybrid vector can also be assembled into a non-integrating particle through the use of an integrase mutant such as the HIV integrase D116N mutant. Such non-integrating vectors can promote the formation of covalently closed circular DNA (called 1-LTR circle and 2-LTR circles) in cells, mimicking the HBV cccDNA.

In another embodiment, an origin of DNA replication such as the OriP/EBNA-1 from EBV (Epstein-Barr virus) or SV40 (SV40 Ori) can be inserted into the vector which will permit the self-duplication of the 1-LTR- or 1-LTR circles with cell division, permitting its persistence in dividing cells.

In another embodiment, the hybrid vector also contains all HBV genes necessary for the assembly of HBV viron particles. If no retro- or lenti-viral packing plasmids were provided, the hybrid vector will be able to assemble HBV particles when transfected into suitable cells such as hepatocytes. When retro- or lenti-viral packaging plasmids were provided with the hybrid vector, both retro- or lenti-viral particles and HBV particles will be assembled in the system, generating two types of virion particles.

In another embodiment, the hybrid vector is embedded into a cell's genome. Cells harboring the Retro- or Lenti-viral HBV hybrid DNA construct can be used as a platform for constitutive production of HBV viral particles, or can be used as a platform for anti-HBV drug screening. The Retro- or Lenti-HBV hybrid genome can also be defective in HBV genes such as the HBV X gene or the P gene. These defects can be complemented by providing the X gene or the P gene through DNA transfection or viral vector delivery of a DNA construct expressing the X or the P gene. Such systems can be used to screen drugs against the X or the P protein.

All technical terms in this description are commonly used in biochemistry, molecular biology and Virology, respectively, and can be understood by those skilled in the field of this invention. Those technical terms can be found in: MOLECULAR CLONING: A LABORATORY MANUAL, 3rd ed., vol. 1-3, ed. Sambrook and Russel, Cold Spring Harbor Laboratory Press, Cold Spring Harbor, N.Y., 2001; CURRENT PROTOCOLS IN MOLECULAR BIOLOGY, ed. Ausubel et al., Greene Publishing Associates and Wiley-Interscience, New York, 1988 (with periodic updates); SHORT PROTOCOLS IN MOLECULAR BIOLOGY: A COMPENDIUM OF METHODS FROM CURRENT PROTOCOLS IN MOLECULAR BIOLOGY, 5.sup.th ed., vol. 1-2, ed. Ausubel et al., John Wiley & Sons, Inc., 2002; GENOME ANALYSIS: A LABORATORY MANUAL, vol. 1-2, ed. Green et al., Cold Spring Harbor Laboratory Press, Cold Spring Harbor, N.Y., 1997; CELLULAR AND MOLECULAR IMMUNOLOGY, 4.sup.th ed. Abbas et al., WB Saunders, 1994. FIELDS VIROLOGY, by Knip, David M. published by Lippincott Williams & Wilkins, 6$^{th}$, 2-volume set edition (2013).

Illustrative Examples are presented below. They are exemplary and non-limiting.

Figure 7:
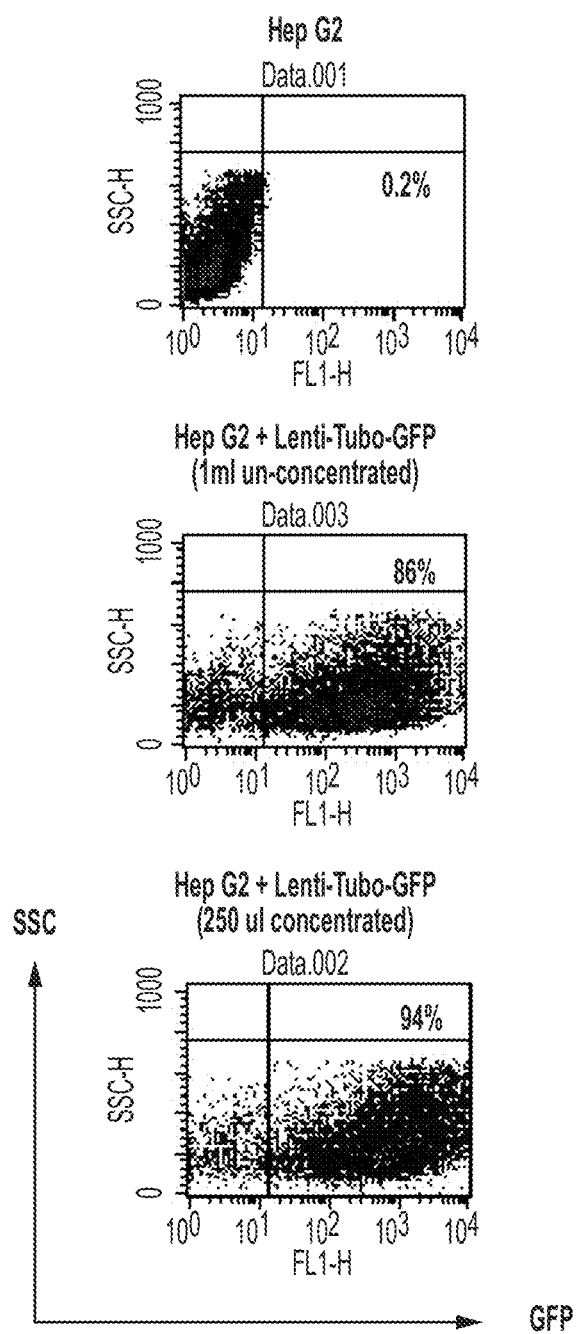
FIG. 7: The hepatocyte HepG2 cell line is highly susceptible for lenti-viral particle transduction. As exemplified here, HepG2 cells were transduced with a lenti-viral particle carrying the GFP (green fluorescent protein) gene. Cells was transduced with an aliquot of either un-concentrated viral particles or concentrated viral particles. GFP express was measured by flow cytometry. Shown are over 90% cells being successfully transduce by the lenti-viral particles.

Example 1: High Efficiency to Deliver Genes into a Liver Cell Line, HepG2, by Lentiviral Vector As exemplified in FIG. 7, the lenti-viral particles can effectively deliver a gene (here is the GFP gene, green fluorescent protein) into hepatocytes such as HepG2 cell.

Figure 8:
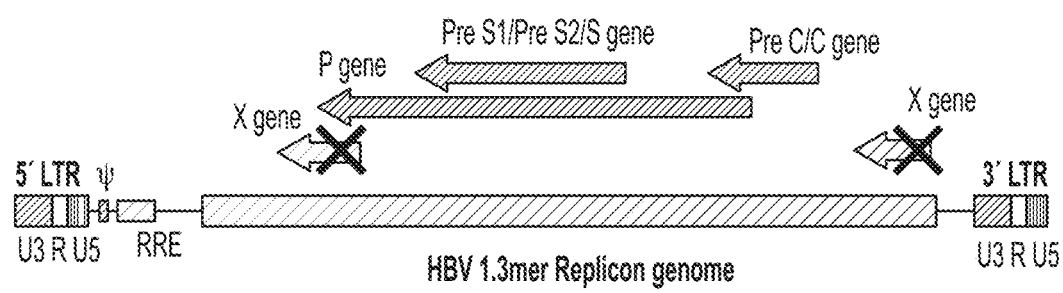
FIG. 8: The genome structure and DNA sequence of the Lenti-HBVΔX hybrid vector that is designed and produced.

Example 2: The Genome Structure and DNA Sequence of a Lenti-Viral HBV Hybrid Vector As exampled in FIG. 8, a lenti-viral HBVΔX hybrid vector is constructed. The vector carries the HBV X gene mutation. This vector can be assembled into a lenti-viral particle to deliver the X gene mutant HBV genome into hepatocytes such as HepG2 cells for screening of anti-HBV X protein drugs.

pLenti-HBVΔX (SEQ ID: 1)

5'CTGCAGTGGAAGGGCTAATTTGGTCCCAAAAAAGACAAGAGATCCTTG

ATCTGTGGATCTACCACACACAAGGCTACTTCCCTGATTGGCAGAACTAC

ACACCAGGGCCAGGGATCAGATATCCACTGACCTTTGGATGGTGCTTCAA

GTTAGTACCAGTTGAACCAGAGCAAGTAGAAGAGGCCAAATAAGGAGAGA

AGAACAGCTTGTTACACCCTATGAGCCAGCATGGGATGGAGGACCCGGAG

```
GGAGAAGTATTAGTGTGGAAGTTTGACAGCCTCCTAGCATTTCGTCACAT
GGCCCGAGAGCTGCATCCGGAGTACTACAAAGACTGCTGACATCGAGCTT
TCTACAAGGGACTTTCCGCTGGGGACTTTCCAGGGAGGTGTGGCCTGGGC
GGGACTGGGGAGTGGCGAGCCCTCAGATGCTACATATAAGCAGCTGCTTT
TTGCCTGTACTGGGTCTCTCTGGTTAGACCAGATCTGAGCCTGGGAGCTC
TCTGGCTAACTAGGGAACCCACTGCTTAAGCCTCAATAAAGCTTGCCTTG
AGTGCTCAAAGTAGTGTGTGCCCGTCTGTTGTGTGACTCTGGTAACTAGA
GATCCCTCAGACCCTTTTAGTCAGTGTGGAAAATCTCTAGCAGTGGCGCC
CGAACAGGGACTTGAAAGCGAAAGTAAAGCCAGAGGAGATCTCTCGACGC
AGGACTCGGCTTGCTGAAGCGCGCACGGCAAGAGGCGAGGGGCGGCGACT
GGTGAGTACGCCAAAAATTTTGACTAGCGGAGGCTAGAAGGAGAGAGATG
GGTGCGAGAGCGTCAGTATTAAGCGGGGGAGAATTAGATCGCGATGGGAA
AAAATTCGGTTAAGGCCAGGGGGAAAGAAAAAATATAAATTAAAACATAT
AGTATGGGCAAGCAGGGAGCTAGAACGATTCGCAGTTAATCCTGGCCTGT
TAGAAACATCAGAAGGCTGTAGACAAATACTGGGACAGCTACAACCATCC
CTTCAGACAGGATCAGAAGAACTTAGATCATTATATAATACAGTAGCAAC
CCTCTATTGTGTGCATCAAAGGATAGAGATAAAAGACACCAAGGAAGCTT
TAGACAAGATAGAGGAAGAGCAAAACAAAAGTAAGACCACCGCACAGCAA
GCGGCCGCTGATCTTCAGACCTGGAGGAGGAGATATGAGGGACAATTGGA
GAAGTGAATTATATAAATATAAAGTAGTAAAAATTGAACCATTAGGAGTA
GCACCCACCAAGGCAAAGAGAAGAGTGGTGCAGAGAGAAAAAAGAGCAGT
GGGAATAGGAGCTTTGTTCCTTGGGTTCTTGGGAGCAGCAGGAAGCACTA
TGGGCGCAGCGTCAATGACGCTGACGGTACAGGCCAGACAATTATTGTCT
GGTATAGTGCAGCAGCAGAACAATTTGCTGAGGGCTATTGAGGCGCAACA
GCATCTGTTGCAACTCACAGTCTGGGGCATCAAGCAGCTCCAGGCAAGAA
TCCTGGCTGTGGAAAGATACCTAAAGGATCAACAGCTCCTGGGGATTTGG
GGTTGCTCTGGAAAACTCATTTGCACCACTGCTGTGCCTTGGAATGCTAG
TTGGAGTAATAAATCTCTGGAACAGATTTGGAATCACACGACCTGGATGG
AGTGGGACAGAGAAATTAACAATTACACAAGCTTAATACACTCCTTAATT
GAAGAATCGCAAAACCAGCAAGAAAAGAATGAACAAGAATTATTGGAATT
AGATAAATGGGCAAGTTTGTGGAATTGGTTTAACATAACAAATTGGCTGT
GGTATATAAAATTATTCATAATGATAGTAGGAGGCTTGGTAGGTTTAAGA
ATAGTTTTTGCTGTACTTTCTATAGTGAATAGAGTTAGGCAGGGATATTC
ACCATTATCGTTTCAGACCCACCTCCCAACCCCGAGGGGACCCGACAGGC
CCGAAGGAATAGAAGAAGAAGGTGGAGAGAGAGACAGAGACAGATCCATT
CGATTAGTGAACGGATCTCGACGGTATCGTATGGGATTGGTGGCGACGA
CTCCTGGAGCCCGTCAGTATCGGCGGAATTCCAGCTGAGCCAGCAGCAGA
TGGGGTGGGAGCAGTATCTCGAGACCGGTAAGCTTGCGGTATCTAGAAGA
TCTCGTACTGAAGGAAAGAAGTCAGAAGGCAAAAACGAGAGTAACTCCAC
AGTAGCTCCGAATTCTTTATAAGGGTCGATGTCCATGCCCCAAAGCCACC

CAAGGCACAGCTTGGAGGCTTGAACAGTAGGACATGAACAAGAGATGATT
AGGCAGAGGTGAAAAAGTTGCATGGTGCTGGTGCGCAGACCAATTTATGC
CTACAGCCTCCTAGTACAAAGACCTTTAACCTAATCTCCTCCCCCAACTC
CTCCCAGTCTTTAAACAAACAGTCTTTGAAGTATGCCTCAAGGTCGGTCG
TTGACATTGCTGAGAGTCCAAGAGTCCTCTTATGTAAGACCTTGGGCAAT
ATTTGGTGGGCGTTCACGGTGGTCTCCATGCGACGTGCAGAGGTGAAGCG
AAGTGCACACGGTCCGGCAGATGAGAAGGCACAGACGGGGAGTCCGCGTA
AAGAGAGGTGCGCCCCGTGGTCGGTCGGAACGGCAGACGGAGAAGGGGAC
GAGAGAGTCCCAAGCGACCCCGAGAAGGGTCGTCCGCAGGATTCAGCGCC
GACGGGACGTAAACAAAGGACGTCCCGCGCAGGATCCAGTTAGCAGCACA
GCCTAGCAGCCATGGAAACGATGTATATTTGCGGGATAGGACAACAGAGT
TATCAGTCCCGATAATGTTTGCTCCAGACCTGCTGCGAGCAAAACAAGCG
GCTAGGAGTTCCGCAGTATGGATCGGCAGAGGAGCCGAAAAGGTTCCACG
CATGCGCTGATGGCCCATGACCAAGCCCCAGCCAGTGGGGGTTGCGTCAG
CAAACACTTGGCACAGACCTGGCCGTTGCCGGGCAACGGGGTAAAGGTTC
AGGTATTGTTTACACAGAAAGGCCTTGTAAGTTGGCGAGAAAGTGAAAGC
CTGCTTAGATTGAATACATGCATACAAAGGCATCAACGCAGGATAACCAC
ATTGTGTAAAAGGGGCAGCAAAACCCAAAAGACCCACAATTCGTTGACAT
ACTTTCCAATCAATAGGCCTGTTAATAGGAAGTTTTCTAAAACATTCTTT
GATTTTTTGTATGATGTGTTCTTGTGGCAAGGACCCATAACATCCAATGA
CATAACCCATAAAATTTAGAGAGTAACCCCATCTCTTTGTTTTGTTAGGG
TTTAAATGTATACCCAAAGACAAAAGAAAATTGGTAACAGCGGTAAAAAG
GGACTCAAGATGCTGTACAGACTTGGCCCCCAATACCACATCATCCATAT
AACTGAAAGCCAAACAGTGGGGGAAAGCCCTACGAACCACTGAACAAATG
GCACTAGTAAACTGAGCCAGGAGAAACGGGCTGAGGCCCACTCCCATAGG
AATTTTCCGAAAGCCCAGGATGATGGGATGGGAATACAGGTGCAATTTCC
GTCCGAAGGTTTGGTACAGCAACAGGAGGGATACATAGAGGTTCCTTGAG
CAGTAGTCATGCAGGTCCGGCATGGTCCCGTGCTGGTTGTTGAGGATCCT
GGAATTAGAGGACAAACGGGCAACATACCTTGATAGTCCAGAAGAACCAA
CAAGAAGATGAGGCATAGCAGCAGGATGAAGAGGAAGATGATAAAACGCC
GCAGACACATCCAGCGATAACCAGGACAAGTTGGAGGACAAGAGGTTGGT
GAGTGATTGGAGGTTGGGGACTGCGAATTTTGGCCAAGACACACGGTAGT
TCCCCCTAGAAAATTGAGAGAAGTCCACCACGAGTCTAGACTCTGCGGTA
TTGTGAGGATTCTTGTCAACAAGAAAAACCCCGCCTGTAACACGAGAAGG
GGTCCTAGGAATCCTGATGTGATGTTCTCCATGTTCAGCGCAGGGTCCCC
AATCCTCGAGAAGATTGACGATAAGGGAGAGGCAGTAGTCAGAACAGGGT
TTACTGTTCCTGAACTGGAGCCACCAGCAGGGAAATACAGGCCTCTCACT
CTGGGATCTTGCAGAGTTTGGTGGAAGGTTGTGGAATTCCACTGCATGGC
CTGAGGATGAGTGTTTCTCAAAGGTGGAGACAGCGGGGTAGGCTGCCTTC
CTGACTGGCGATTGGTGGAGGCAGGAGGCGGATTTGCTGGCAAAGTTTGT
AGTATGCCCTGAGCCTGAGGGCTCCACCCCAAAAGGCCTCCGTGCGGTGG
```

GGTGAAACCCAGCCCGAATGCTCCAGCTCCTACCTTGTTGGCGTCTGGCC
AGGTGTCCTTGTTGGGATTGAAGTCCCAATCTGGATTTGCGGTGTTTGCT
CTGAAGGCTGGATCCAACTGGTGGTCGGGAAAGAATCCCAGAGGATTGCT
GGTGGAAAGATTCTGCCCCATGCTGTAGATCTTGTTCCCAAGAATATGGT
GACCCACAAAATGAGGCGCTATGTGTTGTTTCTCTCTTATATAATATACC
CGCCTTCCATAGAGTGTGTAAATAGTGTCTAGTTTGGAAGTAATGATTAA
CTAGATGTTCTGGATAATAAGGTTTAATACCCTTATCCAATGGTAAATAT
TTGGTAACCTTTGGATAAAACCTGGCAGGCATAATCAATTGCAATCTTCT
TTTCTCATTAACTGTGAGTGGGCCTACAAACTGTTCACATTTTTTGATAA
TGTCTTGGTGTAAATGTATATTAGGAAAAGATGGTGTTTTCCAATGAGGA
TTAAAGACAGGTACAGTAGAAGAATAAAGCCCAGTAAAGTTCCCCACCTT
ATGAGTCCAAGGAATACTAACATTGAGATTCCCGAGATTGAGATCTTCTG
CGACGCGGCGATTGAGACCTTCGTCTGCGAGGCGAGGGAGTTCTTCTTCT
AGGGGACCTGCCTCGTCGTCTAACAACAGTAGTCTCCGGAAGTGTTGATA
GGATAGGGGCATTTGGTGGTCTATAAGCTGGAGGAGTGCGAATCCACACT
CCGAAAGACACCAAATACTCTATAACTGTTTCTCTTCCAAAAGTGAGACA
AGAAATGTGAAACCACAAGAGTTGCCTGAACTTTAGGCCCATATTAGTGT
TGACATAACTGACTACTAGGTCTCTAGACGCTGGATCTTCCAAATTAACA
CCCACCCAGGTAGCTAGAGTCATTAGTTCCCCCCAGCAAAGAATTGCTTG
CCTGAGTGCAGTATGGTGAGGTGAACAATGCTCAGGAGACTCTAAGGCTT
CCCGATACAGAGCTGAGGCGGTATCTAGAAGATCTCGTACTGAAGGAAAG
AAGTCAGAAGGCAAAAACGAGAGTAACTCCACAGTAGCTCCAAATTCTTT
ATAAGGGTCGATGTCCATGCCCCAAAGCCACCCAAGGCACAGCTTGGAGG
CTTGAACAGTAGGACATGAACAAGAGATGATTAGGCAGAGGTGAAAAGT

TGCATGGTGCTGGTGCGCAGACCAATTTATGCCTACAGCCTCCTAGTACA
AAGACCTTTAACCTAATCTCCTCCCCCAACTCCTCCCAGTCTTTAAACAA
ACAGTCTTTGAAGTATGCCTCAAGGTCGGTCGTTGACATTGCTGAGAGTC
CAAGAGTCCTCTTATGTAAGACCTTGGGCAATATTTAGTGGGCGTTCACG
GTGGTCTCCATGCGACGTGCAGAGGTGAAGCGAAGTGCACACGGTCCGGC
AGATGAGAAGGCACAGACGGGGAGTCCGCGTAAAGAGAGGTGCGCCCCGT
GGTCGGTCGGAACGGCAGACGGAGAAGGGGACGAGAGAGTCCCAAGCGAC
CCCGAGAAGGGTCGTCCGCAGGATTCAGCGCCGACGGGACGTAAACAAAG
GACGTCCCGCGCAGGATCCAGTTAGCAGCACAGCCTAGCAGCCATGGAAA
CGATGTATATTTGCGGGATAGGCAACAGAGTTATCAGTCCCGATAATGT
TTGCTCCAGACCTGCTGCGAGCAAAACAAGCGGCTAGGAGTTCCGCAGTA
TGGATCGGCAGAGGAGCCGAAAAGGTTCCACGCATGCGCTGATGGCCCAT
GACCAAGCCCCAGCCAGTGGGGGTTGCGTCAGCAAACACTTGGCACAGAC
CTGGCCGTTGCCGGGCAACGGGGTAAAGGTTCAGGTATTGTTTACACAGA
AAGGCCTTGTAAGTTGGCGAGAAAGTGAAAGCCTGCTTAGATTGAATACG
AGCTCGCTAGCACCTAGAAAAACATGGAGCAATCACAAGTAGCAATACAG
CAGCTAACAATGCTGCTTGTGCCTGGCTAGAAGCACAAGAGGAGGAAGAG
GTGGGTTTTCCAGTCACACCTCAGGTACCTTTAAGACCAATGACTTACAA
GGCAGCTGTAGATCTTAGCCACTTTTTAAAAGAAAAGGGGGGACTGGAAG
GGCTAATTTGGTCCCAAAAAGACAAGAGATCCTGCTGCTTTTTGCCTGT
ACTGGGTCTCTCTGGTTAGACCAGATCTGAGCCTGGGAGCTCTCTGGCTA
ACTAGGGAACCCACTGCTTAAGCCTCAATAAAGCTTGCCTTGAGTGCTCA
AAGTAGTGTGTGCCCGTCTGTTGTGTGACTCTGGTAACTAGAGATCCCTC
AGACCCTTTTAGTCAGTGTGGAAAATCTCTAGCACTGCAG3'

---

What is claimed is:

1. A retro- or lenti-viral HBV (hepatitis B virus) hybrid vector, comprising a HBV genome, wherein said hybrid vector is transcribed 3'-5', and comprises a HIV 5' LTR (long terminal repeat), ψ HIV genome packaging signal, HIV RRE (Rev-dependent element), and at least one of HIV 3' LTR (long terminal repeat) or HIV 3' SIN LTR (self-inactivating LTR with ΔU3 deletion).

2. A retro- or lenti-viral HBV (hepatitis B virus) hybrid vector, comprising a HBV genome, wherein said hybrid vector is transcribed 3'-5', and comprises a HIV 5' LTR (long terminal repeat), ψ HIV genome packaging signal, HIV RRE (Rev-dependent element), and at least one of HIV 3' LTR (long terminal repeat) or HIV 3' SIN LTR (self-inactivating LTR with ΔU3 deletion), wherein said vector comprises a HBV genome with one or more mutations useful for detecting an anti-HBV drug target or therapeutic.

3. The hybrid vector of claim 2, wherein said mutation occurs in the X gene or the S gene.

4. A hepatocyte cell line comprising the hybrid vector of claim 2.

5. A method for delivering a HBV genome into a cell, comprising introducing the retro- or lenti-viral HBV (hepatitis B virus) hybrid vector of claim 2 into said cell, wherein said vector comprises said HBV genome.

6. The method of claim 5, wherein said cell is a liver cell.

7. A hepatocyte cell line comprising the hybrid vector of claim 1.

8. A method for delivering a HBV genome into a cell, comprising introducing the retro- or lenti-viral HBV (hepatitis B virus) hybrid vector of claim 1 into said cell, wherein said vector comprises said HBV genome.

9. The method of claim 8, wherein said cell is a liver cell.

* * * * *

SEQUENCE LISTING

<160> NUMBER OF SEQ ID NOS: 1

<210> SEQ ID NO 1
<211> LENGTH: 6688
<212> TYPE: DNA
<213> ORGANISM: Hepatitis B virus

<400> SEQUENCE: 1

```
ctgcagtgga agggctaatt tggtcccaaa aaagacaaga gatccttgat ctgtggatct    60
accacacaca aggctacttc cctgattggc agaactacac accagggcca gggatcagat   120
atccactgac ctttggatgg tgcttcaagt tagtaccagt tgaaccagag caagtagaag   180
aggccaaata aggagagaag aacagcttgt tacaccctat gagccagcat gggatggagg   240
acccggaggg agaagtatta gtgtggaagt ttgacagcct cctagcattt cgtcacatgg   300
cccgagagct gcatccggag tactacaaag actgctgaca tcgagctttc tacaagggac   360
tttccgctgg ggactttcca ggaggtgtg gcctgggcgg gactggggag tggcgagccc    420
tcagatgcta catataagca gctgcttttt gcctgtactg ggtctctctg gttagaccag   480
atctgagcct gggagctctc tggctaacta gggaacccac tgcttaagcc tcaataaagc   540
```

```
ttgccttgag tgctcaaagt agtgtgtgcc cgtctgttgt gtgactctgg taactagaga    600
tccctcagac ccttttagtc agtgtggaaa atctctagca gtggcgcccg aacagggact    660
tgaaagcgaa agtaaagcca gaggagatct ctcgacgcag gactcggctt gctgaagcgc    720
gcacggcaag aggcgagggg cggcgactgg tgagtacgcc aaaaattttg actagcggag    780
gctagaagga gagagatggg tgcgagagcg tcagtattaa gcgggggaga attagatcgc    840
gatgggaaaa aattcggtta aggccagggg gaaagaaaaa atataaatta aaacatatag    900
tatgggcaag cagggagcta gaacgattcg cagttaatcc tggcctgtta gaaacatcag    960
aaggctgtag acaaatactg ggacagctac aaccatccct tcagacagga tcagaagaac   1020
ttagatcatt ataataca gtagcaaccc tctattgtgt gcatcaaagg atagagataa     1080 aagcaccaa ggaagcttta gacaagatag aggaagagca aaacaaaagt aagaccaccg    1140
cacagcaagc ggccgctgat cttcagacct ggaggaggag atatgaggga caattggaga   1200
agtgaattat ataatataa agtagtaaaa attgaaccat taggagtagc acccaccaag    1260
gcaaagagaa gagtggtgca gagagaaaaa agagcagtgg gaataggagc tttgttcctt   1320
gggttcttgg gagcagcagg aagcactatg ggcgcagcgt caatgacgct gacggtacag   1380
gccagacaat tattgtctgg tatagtgcag cagcagaaca atttgctgag ggctattgag   1440
gcgcaacagc atctgttgca actcacagtc tggggcatca agcagctcca ggcaagaatc   1500
ctggctgtgg aaagatacct aaaggatcaa cagctcctgg ggatttgggg ttgctctgga   1560
aaactcattt gcaccactgc tgtgccttgg aatgctagtt ggagtaataa atctctggaa   1620
cagatttgga atcacacgac ctggatggag tgggacagag aaattaacaa ttacacaagc   1680
ttaatacact ccttaattga agaatcgcaa aaccagcaag aaaagaatga acaagaatta   1740
ttggaattag ataaatgggc aagtttgtgg aattggttta cataacaaa ttggctgtgg    1800 tatataaaat tattcataat gatagtagga ggcttggtag gtttaagaat agttttgct    1860 gtactttcta tagtgaatag agttaggcag ggatattcac cattatcgtt tcagacccac   1920
ctcccaaccc cgaggggacc cgacaggccc gaaggaatag aagaagaagg tggagagaga   1980
gacagagaca gatccattcg attagtgaac ggatctcgac ggtatcgtat ggggattggt   2040
ggcgacgact cctggagccc gtcagtatcg gcggaattcc agctgagcca gcagcagatg   2100
gggtgggagc agtatctcga gaccggtaag cttgcggtat ctagaagatc tcgtactgaa   2160
ggaaagaagt cagaaggcaa aaacgagagt aactccacag tagctccgaa ttctttataa   2220
gggtcgatgt ccatgcccca aagccaccca aggcacagct tggaggcttg aacagtagga   2280
catgaacaag agatgattag gcagaggtga aaaagttgca tggtgctggt gcgcagacca   2340
atttatgcct acagcctcct agtacaaaga cctttaacct aatctcctcc ccaactcct    2400 cccagtcttt aaacaaacag tctttgaagt atgccctcaag gtcggtcgtt gacattgctg   2460
agagtccaag agtcctctta tgtaagacct tgggcaatat ttggtgggcg ttcacggtgg   2520
tctccatgcg acgtgcagag gtgaagcgaa gtgcacacgg tccggcagat gagaaggcac   2580
agacggggga tccgcgtaaa gagaggtgcg ccccgtggtc ggtcggaacg gcagacggag   2640
aaggggacga gagagtccca agcgaccccg agaagggtcg tccgcaggat tcagcgccga   2700
cgggacgtaa acaaaggacg tcccgcgcag gatccagtta gcagcacagc ctagcagcca   2760
tggaaacgat gtatatttgc gggataggac aacagagtta tcagtcccga taatgtttgc   2820
tccagacctg ctgcgagcaa aacaagcggc taggagttcc gcagtatgga tcggcagagg   2880
```

```
agccgaaaag gttccacgca tgcgctgatg gcccatgacc aagccccagc cagtgggggt    2940
tgcgtcagca acacttggc acagacctgg ccgttgccgg gcaacggggt aaaggttcag    3000
gtattgttta cacagaaagg ccttgtaagt tggcgagaaa gtgaaagcct gcttagattg    3060
aatacatgca tacaaaggca tcaacgcagg ataaccacat tgtgtaaaag gggcagcaaa    3120
acccaaaaga cccacaattc gttgacatac tttccaatca ataggcctgt aataggaag    3180 ttttctaaaa cattctttga ttttttgtat gatgtgttct tgtggcaagg acccataaca    3240
tccaatgaca taacccataa aatttagaga gtaacccat ctctttgttt tgttagggtt     3300
taaatgtata cccaaagaca aaagaaaatt ggtaacagcg gtaaaaggg actcaagatg    3360 ctgtacagac ttggccccca ataccacatc atccatataa ctgaaagcca acagtgggg    3420 gaaagcccta cgaaccactg aacaaatggc actagtaaac tgagccagga gaaacgggct    3480
gaggcccact cccataggaa ttttccgaaa gcccaggatg atgggatggg aatacaggtg    3540
caatttccgt ccgaaggttt ggtacagcaa caggagggat acatagaggt tccttgagca    3600
gtagtcatgc aggtccggca tggtcccgtg ctggttgttg aggatcctgg aattagagga    3660
caaacgggca atacccttg atagtccaga agaaccaaca agaagatgag gcatagcagc    3720
aggatgaaga ggaagatgat aaaacgccgc agacacatcc agcgataacc aggacaagtt    3780
ggaggacaag aggttggtga gtgattggag gttggggact gcgaattttg gccaagacac    3840
acggtagttc cccctagaaa attgagagaa gtccaccacg agtctagact ctgcggtatt    3900
gtgaggattc ttgtcaacaa gaaaaacccc gcctgtaaca cgagaagggg tcctaggaat    3960
cctgatgtga tgttctccat gttcagcgca gggtccccaa tcctcgagaa gattgacgat    4020
aagggagagg cagtagtcag aacagggttt actgttcctg aactggagcc accagcaggg    4080 aaaatacaggc ctctcactct gggatcttgc agagtttggt ggaaggttgt ggaattccac    4140
tgcatggcct gaggatgagt gtttctcaaa ggtggagaca gcggggtagg ctgccttcct    4200
gactggcgat tggtggaggc aggaggcgga tttgctggca aagtttgtag tatgccctga    4260
gcctgagggc tccaccccaa aaggcctccg tgcggtgggg tgaaacccag cccgaatgct    4320
ccagctccta ccttgttggc gtctggccag gtgtccttgt tgggattgaa gtcccaatct    4380
ggatttgcgg tgtttgctct gaaggctgga tccaactggt ggtcgggaaa gaatcccaga    4440
ggattgctgg tggaaagatt ctgccccatg ctgtagatct tgttcccaag aatatggtga    4500
cccacaaaat gaggcgctat gtgttgtttc tctcttatat aatatacccg ccttccatag    4560
agtgtgtaaa tagtgtctag tttggaagta atgattaact agatgttctg gataataagg    4620
tttaataccc ttatccaatg gtaaatattt ggtaacctt ggataaaacc tggcaggcat     4680
aatcaattgc aatcttcttt tctcattaac tgtgagtggg cctacaaact gttcacattt    4740
tttgataatg tcttggtgta aatgtatatt aggaaaagat ggtgttttcc aatgaggatt    4800
aaagacaggt acagtagaag aataaagccc agtaaagttc cccaccttat gagtccaagg    4860
aatactaaca ttgagattcc cgagattgag atcttctgcg acgcggcgat tgagaccttc    4920
gtctgcgagg cgagggagtt cttcttctag gggacctgcc tcgtcgtcta caacagtag    4980 tctccggaag tgttgatagg ataggggcat tggtggtct ataagctgga ggagtgcgaa     5040
tccacactcc gaaagacacc aaatactcta taactgtttc tcttccaaaa gtgagacaag    5100
aaatgtgaaa ccacaagagt tgcctgaact ttaggcccat attagtgttg acataactga    5160
ctactaggtc tctagacgct ggatcttcca aattaacacc cacccaggta gctagagtca    5220
ttagttcccc ccagcaaaga attgcttgcc tgagtgcagt atggtgaggt gaacaatgct    5280
```

```
caggagactc taaggcttcc cgatacagag ctgaggcggt atctagaaga tctcgtactg    5340
aaggaaagaa gtcagaaggc aaaaacgaga gtaactccac agtagctcca aattctttat    5400
aagggtcgat gtccatgccc caaagccacc caaggcacag cttggaggct tgaacagtag    5460
gacatgaaca agagatgatt aggcagaggt gaaaaagttg catggtgctg gtgcgcagac    5520
caatttatgc ctacagcctc ctagtacaaa gacctttaac ctaatctcct cccccaactc    5580
ctcccagtct ttaaacaaac agtctttgaa gtatgcctca aggtcggtcg ttgacattgc    5640
tgagagtcca agagtcctct tatgtaagac ctgggcaat atttagtggg cgttcacggt    5700
ggtctccatg cgacgtgcag aggtgaagcg aagtgcacac ggtccggcag atgagaaggc    5760
acagacgggg agtccgcgta aagagaggtg cgcccgtgg tcggtcggaa cggcagacgg    5820
agaaggggac gagagagtcc caagcgaccc cgagaagggt cgtccgcagg attcagcgcc    5880
gacgggacgt aaacaaagga cgtcccgcgc aggatccagt tagcagcaca gcctagcagc    5940
catggaaacg atgtatattt gcgggatagg acaacagagt tatcagtccc gataatgttt    6000
gctccagacc tgctgcgagc aaaacaagcg gctaggagtt ccgcagtatg gatcggcaga    6060
ggagccgaaa aggttccacg catgcgctga tggcccatga ccaagcccca gccagtgggg    6120
gttgcgtcag caaacacttg gcacagacct ggccgttgcc gggcaacggg gtaaaggttc    6180
aggtattgtt tacacagaaa ggccttgtaa gttggcgaga aagtgaaagc ctgcttagat    6240
tgaatacgag ctcgctagca cctagaaaaa catggagcaa tcacaagtag caatacagca    6300
gctaacaatg ctgcttgtgc ctggctagaa gcacaagagg aggaagaggt gggttttcca    6360
gtcacacctc aggtaccttt aagaccaatg acttacaagg cagctgtaga tcttagccac    6420
tttttaaaag aaaaggggg actggaaggg ctaatttggt cccaaaaaag acaagagatc    6480
ctgctgcttt ttgcctgtac tgggtctctc tggttagacc agatctgagc ctgggagctc    6540
tctggctaac tagggaaccc actgcttaag cctcaataaa gcttgccttg agtgctcaaa    6600
gtagtgtgtg cccgtctgtt gtgtgactct ggtaactaga gatccctcag accctttag     6660 tcagtgtgga aaatctctag cactgcag                                       6688
```